US007290896B2

(12) United States Patent
Dallas et al.

(10) Patent No.: US 7,290,896 B2
(45) Date of Patent: Nov. 6, 2007

(54) BLOOD TRACKING SYSTEM

(75) Inventors: Edgar A. Dallas, Beaverton, OR (US); Scott C. Hartley, Portland, OR (US); Frederick T. Karl, West Linn, OR (US)

(73) Assignee: Fiskars Brands, Inc., Madison, WI (US)

( * ) Notice: Subject to any disclaimer, the term of this patent is extended or adjusted under 35 U.S.C. 154(b) by 0 days.

(21) Appl. No.: 11/195,371

(22) Filed: Aug. 2, 2005

(65) Prior Publication Data

US 2006/0044792 A1 Mar. 2, 2006

Related U.S. Application Data

(60) Provisional application No. 60/598,289, filed on Aug. 3, 2004.

(51) Int. Cl.
*F21L 7/00* (2006.01)
*F21L 4/02* (2006.01)

(52) U.S. Cl. ....................... 362/184; 362/231; 362/800

(58) Field of Classification Search ................ 362/184, 362/555, 231, 800
See application file for complete search history.

(56) References Cited

U.S. PATENT DOCUMENTS 5,201,755 A * 4/1993 Klement ..................... 606/194
6,019,482 A * 2/2000 Everett ....................... 362/184
2004/0223342 A1* 11/2004 Klipstein et al. ........... 362/555

* cited by examiner

*Primary Examiner*—Sandra O'Shea
*Assistant Examiner*—James W Cranson, Jr.
(74) *Attorney, Agent, or Firm*—Foley & Lardner LLP

(57) ABSTRACT

A blood tracking system, comprising a light source comprising a first LED configured to emit light of a first color and a second LED configured to emit light of a second color is disclosed. The light of the first color and the light of the second color are mixed to appear as light of a third color when the first LED and the second LED are activated; and wherein the light of a third color is effective for highlighting blood. A method of highlighting a red material comprising illuminating the red material with both red and blue light is also disclosed.

19 Claims, 3 Drawing Sheets

10 36 34 14 30 42 32 44 18 12 16 24 20 26

BLOOD TRACKING SYSTEM

CROSS-REFERENCE TO RELATED PATENT APPLICATIONS

This application claims the benefit of U.S. Provisional Application No. 60/598,289, filed Aug. 3, 2004, entitled "Blood Tracking System," which is incorporated herein by reference in its entirety.

BACKGROUND

The present invention relates generally to the field of blood tracking. In particular, the present invention relates to a portable lighting unit configured to track blood using a light emitting diode (LED) illumination system.

There are occasions in which it is useful to be able to easily identify small amounts of blood in a particular environment. For example, a hunter may wound an animal, such as a deer, that runs some distance away from the hunter after being wounded. In such a case, the hunter would like to follow the blood trail in order to find the animal. Small drops of blood can be difficult to see on the ground and on foliage, especially in low light conditions. To aid the hunter, blood tracking systems have been devised that help differentiate the red color of the blood from the rest of the environment. Such systems include the utilization of special filters placed on flashlights and/or special goggles or glasses that highlight the blood.

It would be advantageous to provide a portable lighting device that gives the user true blood tracking capability in low-level lighting conditions by using the optical principle of color enhancement. In particular, it would be advantageous to provide a lighting device that gives a distinct visual appearance to blood without requiring special filters on a light source or requiring the user to wear special glasses or goggles.

SUMMARY OF THE INVENTION

One embodiment of the invention relates to a blood tracking system, comprising a light source comprising a first LED configured to emit light of a first color and a second LED configured to emit light of a second color. The light of the first color and the light of the second color are mixed to appear as light of a third color when the first LED and the second LED are activated; and wherein the light of a third color is effective for highlighting blood.

Another embodiment of the invention relates to a flashlight for detecting and tracking red objects comprising a housing, a red LED coupled to the housing, a blue LED coupled to the housing, a power source, and an actuator for activating the red LED and the blue LED. The light emitted by the red LED and the light emitted by the blue LED mix to create a magenta spot that is suitable for highlighting red material.

Yet another embodiment of the invention relates to a method of highlighting a red material comprising illuminating the red material with both red and blue light. The red and blue light mix to produce a magenta spot, which when illuminating a red colored material, makes the red material appear orange to the human eye.

DETAILED DESCRIPTION

Figure 3:
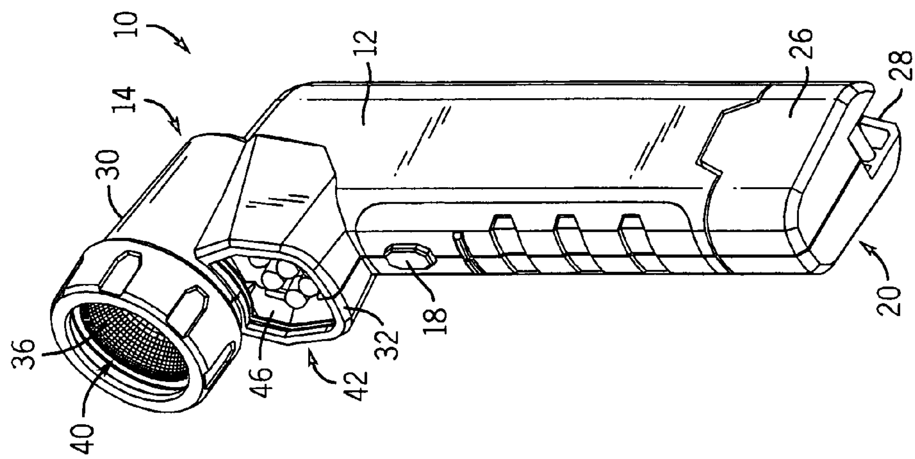
FIG. 3 is a perspective view of a tracking device.

Color perception cannot be attributed directly and solely to wavelengths of light. The eye focuses slightly differently on long wavelengths (reds) than on short wavelengths (blues). According to an exemplary embodiment of the present invention, a tracking device may include a multiple color light source having a red LED light beam and a blue LED light beam that create an illusion causing the eye to see red objects in low level lighting conditions as blaze orange. Simultaneously illuminating a red blood spot with the red LED beam and the blue LED beam of the system creates the desired highlighted orange blood effect. The highlighted blood appears orange and the surrounding background green or brown flora appears blue/purple under the multi color LED beam even when the flora is wet.

In an exemplary embodiment, the blood tracking system is incorporated into a portable light source, such as a headlamp flashlight. The headlamp may have a removable, adjustable headband. The headlamp may utilize a single AAA battery to provide power to the LEDs. Alternatively, multiple batteries may be used and the batteries may be of various sizes and types. The blood tracking system may be utilized in other portable light sources such as handheld flashlights and lanterns.

One headlamp into which the system may be incorporated is a TRACER headlamp, sold by Gerber Legendary Blades, a Fiskars Brands Company. The TRACER headlamp circuitry may be modified to incorporate a red and a blue LED. Trimming resistors, which may be adjusted to provide a desired resistance, may be added to allow for varying the intensity of each LED in order to generate a desired output.

In some embodiments, two distinct colors may be utilized. In an exemplary embodiment, one or more blue LEDs (i.e. LEDs having a peak wavelength centered in the range of about 410 nm to about 500 nm) may be used with one or more red LEDs (i.e. LEDs having a peak wavelength in the range of about 600 nm to about 740 nm) to produce a spot that appears to be magenta to a user. In some embodiments, an LED having an output centered at about 425 nm may be used with an a LED having an output centered at about 625 nm. In another exemplary embodiment, a red LED having a wavelength centered around 628 nm and a blue LED having a wavelength centered around 470 nm may be used.

In some embodiments, the blood tracking system may include two LEDs (a red LED and a blue LED) that are simultaneously activated to provide the desired blood tracking effect. In other embodiments, additional LEDs are used to increase the brightness of the light source, such as two red LEDs and two blue LEDs, or even more LEDs, such as 3-6 red LEDs and 3-6 blue LEDs. The number of red LEDs may be greater or less than the number of blue LEDs. Also, the intensity of the red LEDs may be greater of less than that of the blue LEDs.

In another embodiment, the red LED may be pulsed at a particular frequency, which, when combined with the steady output of the blue LED, can enhance the visual signature of the blood or other red material being tracked.

In some embodiments, the LEDs may be used individually, to provide either red output or blue output separately. In other embodiments, other LEDs may be added to the system, including other LEDs having different colors or wavelengths, such as infrared wavelengths. Circuitry may be utilized to provide different lighting options of the various LEDs and combinations of LEDs.

The tracking device has several potential uses in addition to use in the hunting context described above. For example, the system may have several potential military uses, such as by medics to determine the source of blood on a body that is covered by dirt, mud, or other material obscuring the wound providing the source of blood. Further, special forces personnel may utilize the invention to track enemy combatants that may have been wounded and are providing a blood trail. Also, the tracking device may be used by forensic analysts to find blood.

Figure 2:
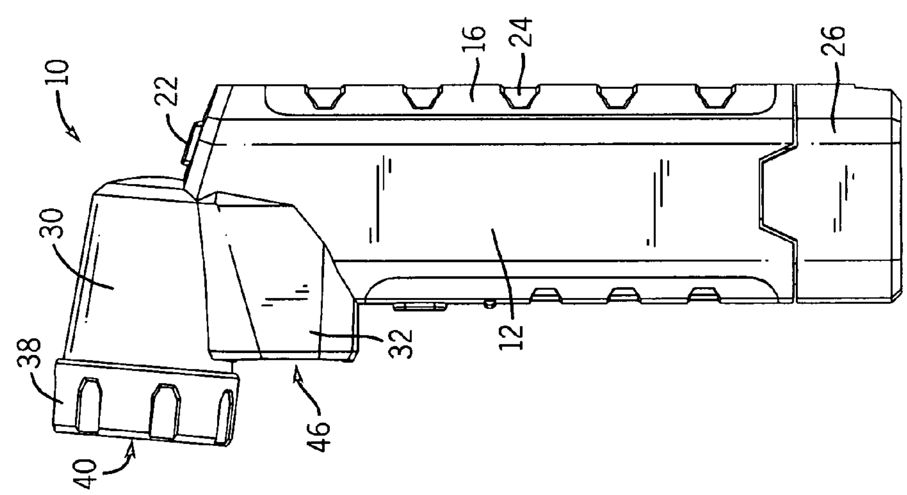
FIG. 2 is a side elevation view of a tracking device.
Figure 1:
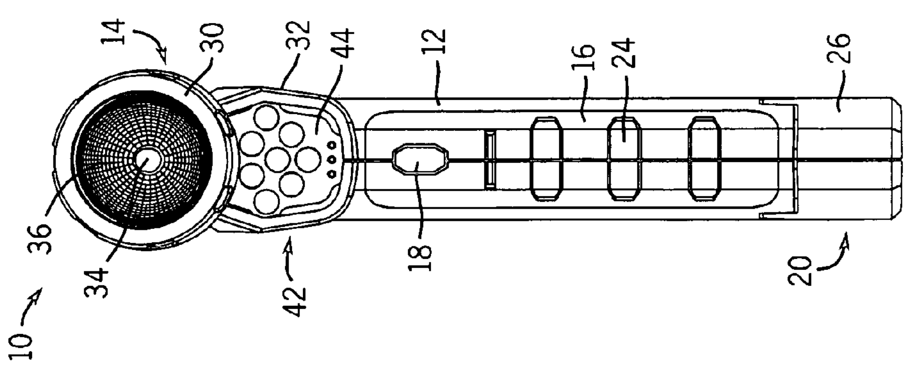
FIG. 1 is a front elevation view of a tracking device.

Referring to FIGS. 1-3, according to an exemplary embodiment, tracking device 10 includes a housing with a handle 12, and a head 14. Handle 12 includes a grip portion 16, first power switch 18, a power supply 20, and a second power switch 22. Head 14 and handle 12 are shown coupled to each other at an angle of about 90° and may be formed as a single unitary body. Alternatively, head 14 and handle 12 may be coupled at other angles or in-line such that the head and handle extend along either the same longitudinal axis, or along longitudinal axes that are substantially parallel. In yet another embodiment, head 14 may be rotatably coupled to handle 12 to allow a user to adjust the angle formed by head 14 and handle 12.

Handle 12 may include a grip portion 16 that includes grooves 24 for the fingers of a user to contact while using tracking device 10. Handle 12 is shown as being generally straight along a longitudinal axis. Alternatively, other ergonomic configurations including a curved handle may be used. Power supply 20 or handle 12 may include a removable cover 26 which may cover a battery compartment. According to some embodiments, tracking device 10 may be adaptable to be used with alternating or direct current from an external power source.

Head 14 may include a primary light source 30 and a secondary light source 32. Primary light source 30 may include a lamp 34, a reflector 36, cap 38, and lens 40. Lamp 34 may be a xenon bulb. Alternatively, lamp 34 may be another type of incandescent bulb, or one or more white LEDs. Reflector 36 may be generally parabolic in shape to direct light emitted from lamp 34 into a beam. Reflector 36 may be faceted or smooth. Primary light source 30 may include a cap 38 for securing the primary light source 30 to head 14. Cap 38 may be threadably or otherwise coupled to head 14. Lens 40 may be disposed within cap 38 to provide a water resistant seal for primary light source 30. According to some embodiments, reflector 36 may be coupled to cap 38 such that rotation of cap 38 moves reflector 36 relative to lamp 34 whereby the width of the light beam produced by primary light source 30 may be adjusted by rotating cap 38. Second power switch 22 may be used to turn primary light source 30 on and off.

Secondary light source 32 may include an LED array 42, shown as eight LEDs of similar size in FIG. 1. A greater or lesser number of LEDs in other configurations may also be used. LED array 42 may be controlled by first power switch 18. In some embodiments, first power switch 18 may simultaneously deactivate primary light source 30 and activate LED array 42.

In some embodiments, tracking device 10 may optionally include a power indicator 44, shown as three LEDs, that may be used to indicate the strength of batteries used to power tracking device 10. Alternatively, a greater or lesser number of LEDs in other configurations may also be used to indicate battery strength. Also, power indicator 44 may be placed in a variety of positions on tracking device 10. Secondary light source 32 may be covered by lens 46 to protect LED array 42 and power indicator 44.

According to some embodiments, removable cover 26 may include an optional coupling point 28 which may be used to attach a lanyard to tracking device 10. Alternatively, a coupling point for a lanyard may be provided elsewhere on tracking device 10.

Figure 4:
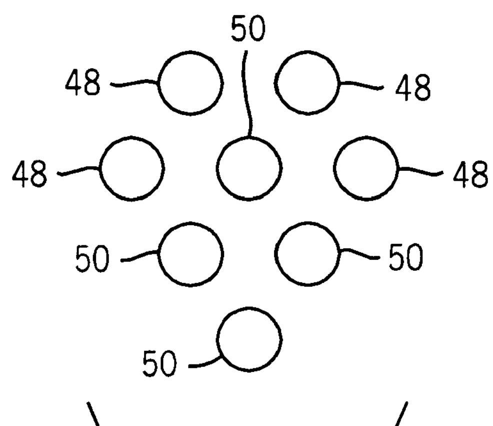
FIG. 4 is an elevation view of an LED array.

Referring to FIG. 4, LED array 42 may include a total of eight LEDs 48 and 50. According to some embodiments, LEDs 48 may be blue while LEDs 50 are red. Alternatively, LEDs 48 may be red while LEDs 50 are blue.

Figure 5:
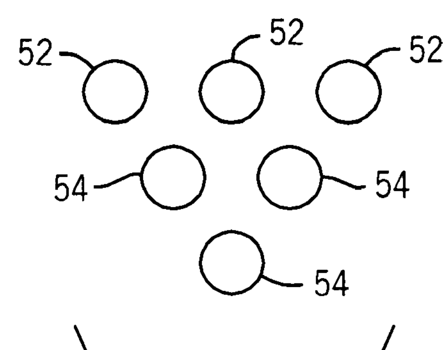
FIG. 5 is an elevation view of an LED array.

Referring to FIG. 5, an LED array for use in a tracking device may include a total of six LEDs. According to some embodiments, LEDs 52 may be blue while LEDs 54 are red. Alternatively, LEDs 52 may be red while LEDs 54 are blue.

Figure 6:
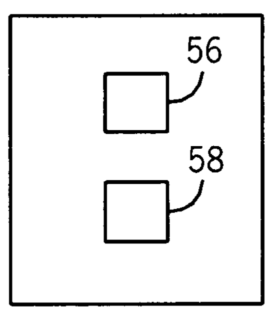
FIG. 6 is an elevation view of an LED array.

Referring to FIG. 6, an LED array for use in a tracking device may include LED dies (i.e. components made of a semiconductor material used to generate light in an LED). According to some embodiments one or more red LED dies 56 may be used with one or more blue LED dies 58. The LED dies may be focused and tuned to produce a homogenous magenta spot.

Figure 7:
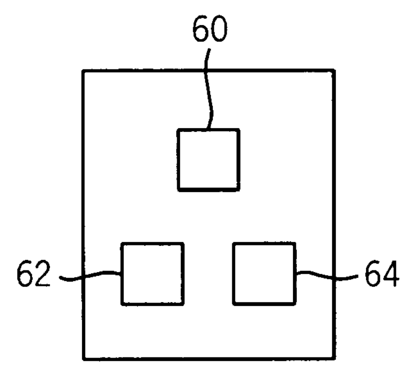
FIG. 7 is an elevation view of an LED array.

Referring to FIG. 7, an LED array for use in a tracking device may alternatively include one or more red LED dies 60 may be used with one or more blue LED dies 62 and one or more green LED dies 64 where the green output is kept to a low level relative to the red and blue outputs to avoid diminishing the highlighting effect of the tracking device.

Figure 8:
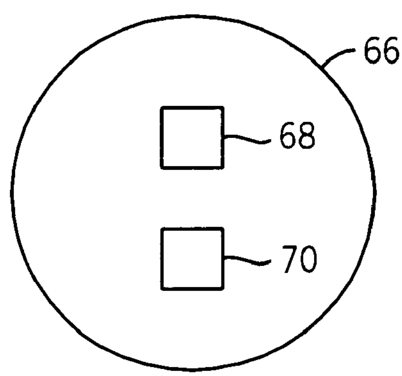
FIG. 8 is an elevation view of an LED array.

Referring to FIG. 8, an LED array for use in a tracking device may include a bicolor LED 66. According to some embodiments one or more red emitter outputs 68 may be used with one or more blue emitter outputs 70. The LED emitter outputs may be focused and tuned to produce a homogenous magenta spot.

Figure 9:
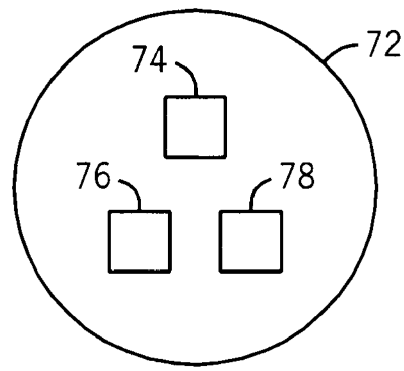
FIG. 9 is an elevation view of an LED array.

Referring to FIG. 9, an LED array for use in a tracking device may include a tricolor LED 72. According to some embodiments, the tricolor LED 72 may include one or more red emitter outputs 74, one or more blue emitter outputs 76, and one or more green emitter outputs 78. The LED emitter outputs may be focused and tuned to produce a homogenous magenta spot.

Figure 10:
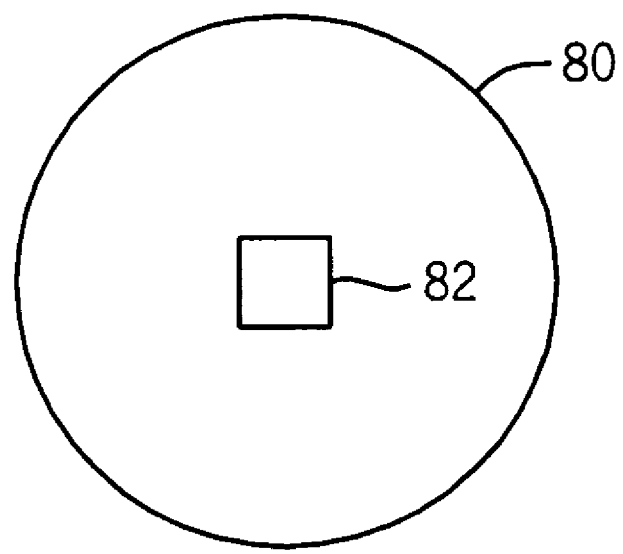
FIG. 10 is an elevation view of an LED array.

Referring to FIG. 10, an LED array for use in a tracking device may include a magenta LED 80. The magenta LED 80 may include an emitter 82 designed to emit a magenta output (i.e. a combination of blue and red wavelengths).

Figure 11:
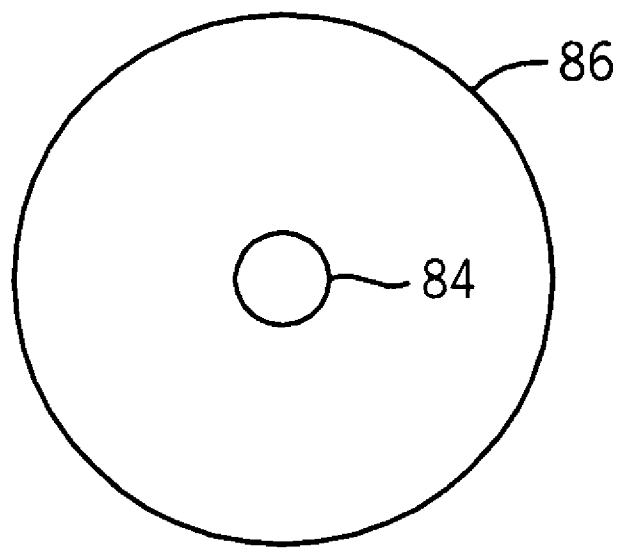
FIG. 11 is an elevation view of an LED array.

Referring to FIG. 11, a white LED 84 may be used with a filter 86. Filter 86 may absorb green light while transmitting and balancing blue and red light to create a magenta beam. Alternatively, a plurality of filters may be used create a magenta beam. In some embodiments, a plurality of light sources, such as white LEDs may be used with filters to create a magenta beam. For example, one light source including one or more white LEDs and a blue filter may be used with a second light source including one or more white LEDs and a red filter.

While the detailed drawings and specific examples given describe various exemplary embodiments of the blood tracking system, they serve the purpose of illustration only. It is to be understood that the invention is not limited in its application to the details of construction and the arrangements of components set forth in the preceding description or illustrated in the drawings. For example, other arrangements of LEDs may be used to create the desired blood tracking effect, or the flashlight may be one of a variety of configurations known in the art. Furthermore, other substitutions, modifications, changes, and omissions may be made in the design, operating conditions, and arrangements of the exemplary embodiments without departing from the scope of the invention as expressed in the appended claims.

What is claimed is:

1. A blood tracking system comprising:

a light source, comprising a first LED configured to emit blue light and a second LED configured to emit red light;

wherein the blue light and the red light are mixed to provide a mixed spot that appears as magenta when the first LED and the second LED are activated; and wherein the mixed spot highlights blood.

2. The blood tracking system of claim 1, further comprising a total of one to six red LEDs and a total of one to six blue LEDs.

3. The blood tracking system of claim 2, comprising an equal number of red and blue LEDs.

4. The blood tracking system of claim 1, wherein the blood tracking system is a handheld flashlight.

5. The blood tracking system of claim 1, wherein the blood tracking system is a headlamp flashlight.

6. The blood tracking system of claim 1, further comprising an additional light source comprising an emitter of white light.

7. The blood tracking system of claim 6, wherein the additional light source further comprises a reflector and a lens.

8. A flashlight for detecting and tracking blood comprising:

a housing;

a red LED coupled to the housing;

a blue LED coupled to the housing;

a power source, and an actuator for activating the red LED and the blue LED;

wherein the light emitted by the red LED and the light emitted by the blue LED mix to create a magenta spot that highlights blood.

9. The flashlight of claim 8, wherein the flashlight is a headlamp flashlight.

10. The flashlight of claim 8, wherein the flashlight is a handheld flashlight.

11. The flashlight of claim 8, wherein the red LED emits light at a peak wavelength in the range of about 600 nm to about 740 nm.

12. The flashlight of claim 8, wherein the blue LED emits light at a peak wavelength in the range of about 410 nm to about 500 nm.

13. The flashlight of claim 8, wherein the red LED emits light about a peak wavelength of about 628 nm, and the blue LED emits light about a peak wavelength of about 470 nm.

14. The flashlight of claim 8, further comprising an additional light source comprising an emitter of white light.

15. The flashlight of claim 14, wherein the additional light source further comprises a reflector and a lens.

16. A method of highlighting a red material comprising:

illuminating the red material with both red and blue light;

wherein the red and blue light are mixed to produce a magenta spot;

whereby the red material is made to appear orange to the human eye.

17. The method of claim 16, wherein the red and blue light is provided by a flashlight comprising a red LED and a blue LED.

18. The method of claim 16, wherein the flashlight is a handheld flashlight.

19. The method of claim 16, wherein the flashlight is a headlamp flashlight.

* * * * *